(12) United States Patent
McInnis et al.

(10) Patent No.: US 10,584,303 B2
(45) Date of Patent: Mar. 10, 2020

(54) STABILIZATION OF ISOTHIAZOLONES IN AQUEOUS COMPOSITIONS

(71) Applicant: DDP Specialty Electronic Materials US, Inc., Wilmington, DE (US)

(72) Inventors: Christine McInnis, Blue Bell, PA (US); Stephen W. King, League City, TX (US)

(73) Assignee: DDP SPECIALTY ELECTRONIC MATERIALS US, INC., Wilmington, DE (US)

( * ) Notice: Subject to any disclaimer, the term of this patent is extended or adjusted under 35 U.S.C. 154(b) by 0 days.

(21) Appl. No.: 15/310,515

(22) PCT Filed: May 1, 2015

(86) PCT No.: PCT/US2015/028796
§ 371 (c)(1),
(2) Date: Nov. 11, 2016

(87) PCT Pub. No.: WO2015/175241
PCT Pub. Date: Nov. 19, 2015

(65) Prior Publication Data
US 2017/0107444 A1    Apr. 20, 2017

Related U.S. Application Data

(60) Provisional application No. 61/994,194, filed on May 16, 2014.

(51) Int. Cl.
| | |
|---|---|
| *C10M 135/36* | (2006.01) |
| *C08F 8/32* | (2006.01) |
| *C10M 159/12* | (2006.01) |
| *C10M 173/02* | (2006.01) |
| *A01N 43/80* | (2006.01) |
| *C10M 141/08* | (2006.01) |
| *C10M 173/00* | (2006.01) |
| *A01N 25/22* | (2006.01) |

(52) U.S. Cl.
CPC .......... *C10M 173/02* (2013.01); *A01N 25/22* (2013.01); *A01N 43/80* (2013.01); *C10M 141/08* (2013.01); *C10M 173/00* (2013.01); *C10M 2215/02* (2013.01); *C10M 2215/042* (2013.01); *C10M 2219/104* (2013.01); *C10N 2230/16* (2013.01); *C10N 2230/66* (2013.01); *C10N 2240/40* (2013.01)

(58) Field of Classification Search
CPC . C10M 133/28; C10M 133/08; C10M 135/32
USPC ................................................... 508/271, 543
See application file for complete search history.

(56) References Cited

U.S. PATENT DOCUMENTS

| | | | |
|---|---|---|---|
| 2003/0232906 A1 | 12/2003 | Ghosh | |
| 2008/0063723 A1 | 3/2008 | Choi et al. | |
| 2008/0280792 A1* | 11/2008 | Williams | ............... A01N 43/80 508/154 |
| 2010/0093736 A1 | 4/2010 | Coburn et al. | |
| 2012/0122094 A1 | 5/2012 | May et al. | |
| 2012/0189603 A1 | 7/2012 | Beilfuss et al. | |

FOREIGN PATENT DOCUMENTS

GB        1191253 A    5/1970

OTHER PUBLICATIONS

Willingham, et al., "Compatibility and Stabilization of Methylchloro/Methyl-Isothiazolone in Metalworking Fluids", J. Soc. Tribologists, pp. 729-732 (1991).

* cited by examiner

*Primary Examiner* — Prem C Singh
*Assistant Examiner* — Francis C Campanell

(57) ABSTRACT

An aqueous composition comprising: (a) at least one 3-isothiazolone; and (b) at least one tertiary amine having three $C_2$-$C_6$ hydroxyalkyl groups, wherein at least one of the hydroxyalkyl groups has a secondary hydroxyl group.

8 Claims, No Drawings

STABILIZATION OF ISOTHIAZOLONES IN AQUEOUS COMPOSITIONS

This invention relates to aqueous compositions, including metalworking fluids, containing isothiazolones and tertiary amine compounds.

A fluid composition containing a 3-isothiazolone and alkanolamines is disclosed in U.S. Pub. No. 2008/0280792. This reference discloses that the 3-isothiazolone needs to be stabilized by addition of iodine-containing stabilizers or mercaptobenzothiazole. However, use of such stabilizers in fluids, including metalworking fluids, is undesirable for economic and environmental reasons.

The problem addressed by this invention is to provide an improved aqueous composition containing 3-isothiazolones and alkanolamines

STATEMENT OF THE INVENTION

The present invention is directed to an aqueous composition comprising: (a) at least one 3-isothiazolone; and (b) at least one tertiary amine comprising three $C_2$-$C_6$ hydroxyalkyl groups, wherein at least one of said hydroxyalkyl groups has a secondary hydroxyl group.

DETAILED DESCRIPTION OF THE INVENTION

"MIT" is 2-methyl-4-isothiazolin-3-one, also referred to by the name 2-methyl-3-isothiazolone. "CMIT" is 5-chloro-2-methyl-4-isothiazolin-3-one, also referred to by the name 5-chloro-2-methyl-3-isothiazolone. Preferably, the weight ratio of CMIT to MIT is at least 2:1, preferably at least 2.5:1. Preferably, the weight ratio of CMIT to MIT is no greater than 4:1, preferably no greater than 3.5:1. In one preferred embodiment of the invention, the CMIT:MIT ratio is about 3:1. "MBIT" is N-methyl-1,2-benzisothiazolin-3-one. "OIT" is 2-octyl-4-isothiazolin-3-one. Preferably, the 3-isothiazolone is MIT, CMIT/MIT, OIT, MBIT or a mixture thereof; preferably MIT and/or OIT.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The following abbreviations are used throughout the specification: ppm=parts per million by weight (weight/weight), mL=milliliter, AI=active ingredient, i.e., total amount of isothiazolones. Unless otherwise specified, temperatures are in degrees centigrade (° C.), references to percentages are percentages by weight (wt %) and amounts and ratios are on an active ingredient basis, unless otherwise specified. When experiments are described as being carried out at "room temperature" this means a temperature from 20-25° C.

Aqueous compositions include, e.g., metalworking fluids and concentrates, household products (e.g., cleaners), personal care products (e.g., cream, lotions, hair care products), aqueous coatings compositions (e.g., latex paints), wood treatment compositions and fabric treatment compositions. Preferably, the aqueous composition is a metalworking fluid or a metalworking fluid concentrate. Typically concentrates are diluted for use as metalworking fluids. Preferably, the concentration of an ingredient (other than water) in the concentrate is from 10 to 100, preferably 10 to 25 times the concentration of the same ingredient in the metalworking fluid. The aqueous composition may also contain one or more metalworking additives, which include, e.g., amines other than the tertiary amines described herein, fatty acids, surfactants, soluble oils, emulsifiable oils, oiliness agents (to increase film strength e.g., polyol esters), synthetic lubricants (to improve lubricity of fluid e.g., ethylene oxide-propylene oxide random or copolymers, oil soluble polyalkylene ethers), emulsifiers (to improve wetting or dispersing of oil in water e.g., fatty amides, salts of fatty acids, nonionic surfactants), extreme pressure agents (for lubrication under high pressure e.g., sulfurized fatty materials, chlorinated paraffins, phosphorus derivatives, etc.), coupling agents (to improve the solubility of the various additives in the MWF e.g., fatty alcohols), corrosion inhibitors (to prevent part or tool corrosion e.g., amine salts of carboxylic acids, or boric acid), defoamers (to reduce foam e.g., long chain fatty alcohols, silicones, siloxanes), metal passivators (protection of newly exposed metal from corrosion e.g., triazoles), anti-mist additives (alkylphenol alkoxylates) and chelators (to reduce hard water effects, e.g., EDTA, phosphates, polyphosphates).

The hydroxyalkyl groups in the tertiary amine may be the same or different. Preferably, two of the hydroxyalkyl groups have a secondary hydroxyl group. Preferably, the tertiary amine has three $C_2$-$C_5$ hydroxyalkyl groups, preferably three $C_2$-$C_4$ hydroxyalkyl groups, preferably three hydroxyalkyl groups each of which is a $C_2$ or $C_4$ hydroxyalkyl group. Preferably, $C_2$ hydroxyalkyl groups are 2-hydroxyethyl groups. Preferably, $C_3$ hydroxyalkyl groups are 2-hydroxy-1-propyl groups. Preferably, $C_4$ hydroxyalkyl groups are 2-hydroxy-1-butyl groups. Especially preferred amines include N,N-bis(2-hydroxybutyl)-2-aminoethanol, 1-[bis(2-hydroxyethyl)amino]-2-butanol and triisopropanol amine (TIPA, CAS no. 122-20-3).

Preferably, the aqueous composition contains at least 1 ppm of 3-isothiazolone(s) (on an active ingredient basis), preferably at least 3 ppm, preferably at least 5 ppm, preferably at least 10 ppm, preferably at least 50 ppm, preferably at least 100 ppm, preferably at least 500 ppm; preferably the composition contains no more than 6,000 ppm, preferably no more than 4,000 ppm, preferably no more than 3,000 ppm, preferably no more than 2,000 ppm, preferably no more than 1,000 ppm, preferably no more than 500 ppm. Preferably, the aqueous composition contains at least 0.1 wt % of tertiary amine(s), preferably at least 0.5 wt %, preferably at least 1 wt %, preferably at least 2 wt %, preferably at least 3 wt %, preferably at least 5 wt %; preferably the composition contains no more than 35 wt %, preferably no more than 30 wt %, preferably no more than 25 wt %, preferably no more than 20 wt %, preferably no more than 15 wt %, preferably no more than 10 wt %. The aqueous composition preferably contains at least 30 wt % water, preferably at least 40 wt %, preferably at least 50 wt %, preferably at least 60 wt %, preferably at least 70 wt %; preferably no more than 99 wt % water, preferably no more 97 wt %, preferably no more than 95 wt %, preferably no more than 90 wt %, preferably no more than 80 wt %.

Preferably, the aqueous composition is substantially free of bromic acid, iodic acid, periodic acid or their salts and mercaptobenzothiazole, i.e., the composition contains less than 0.05% total of these substances, preferably less than 0.01%, preferably less than 0.005%, preferably less than 0.001%.

EXAMPLES

Hydroxyl Content—Hydroxyl content was measured by derivatization of the amine alkoxylate with an excess of phthalic anhydride reagent with imidazole catalyst in pyridine solvent at 100° C. for 30 min using a procedure based on ASTM D 4274. After formation of the phthalate half ester, the unreacted phthalic anhydride was hydrolyzed and titrated with 1 N sodium hydroxide reagent using a Mettler DL-55 titrator. The half ester was quantified by the difference between the sample titration and a blank titration of the same amount of phthalic anhydride reagent completely hydrolyzed with water. The difference is expressed as hydroxyl number (mg KOH/g sample) or % OH. For the amine butoxylates (functionality=3) analyzed in this study, the molecular weight is calculated by the following formula: (3×1700)/% OH.

H-1 NMR—The amine butoxylate sample in chloroform-d was prepared in a 5 mm NMR tube. The data were collected by a PROTON experiment on a BRUKER 300 MHz NMR.

Synthesis of Monoethanolamine (MEA) and Diethanolamine (DEA) Butoxylates

All of the alkoxylation reactions were performed in a jacketed, baffled 9 L stainless steel autoclave reactor equipped with a magnetically driven impeller, pressure transducer, jacket return line thermocouple, and redundant reactor thermocouples. Temperature control was achieved with a mixture of steam and cooling water to the reactor jacket introduced via control valves operated by the MOD-V digital control system. Butylene oxide (BO) was charged into a designated feed tank situated on a scale. BO was metered from the feed tank bottom outlet to the reactor through an automated flow control valve within the operating temperature (±5° C. of set point) and pressure (16-85 psia) constraints. These runs targeted the butoxylation of MEA with 2 BO equivalents and DEA with 1 BO equivalent.

Monoethanolamine and Diethanolamine were obtained from Aldrich. Dow butylene oxide was obtained from the Freeport Market Development Plant.

Preparation of MEA Dibutoxylate
(N,N-bis(2-hydroxybutyl)-2-aminoethanol)

This run targeted the butoxylation (2 BO) of Monoethanolamine (MEA) without addition of catalyst (amine autocatalytic) using a 110° C. feed temperature and a 110° C. digest temperature. MEA (901.7 g) was charged to a 9 L reactor. The reactor was pressurized with nitrogen and vented (7 times) to remove atmospheric oxygen. Subsequently, the reactor was pressurized with nitrogen to 16-20 psia at ambient temperature. The reactor contents were heated with agitation at 110° C., then BO (2180 g total) was metered into the reactor over 4 hr at 110° C. resulting in an operating pressure of 30 psia. After the BO feed was complete, the reactor contents were agitated at 110° C. for an additional 10 hr (overnight) to consume unreacted oxide (digest). The reactor was cooled to approximately 100° C., then nitrogen sparged for 1 hr to remove any unreacted butylene oxide. Subsequently, the reactor was cooled to 60° C. and drained affording 3056.1 g of product. A sample of the reaction product analyzed by hydroxyl titration (25.228% OH corresponding to 202 MW or MEA+2.0BO). Proton NMR spectroscopy provided an estimated BO:MEA molar ratio of 2.1.

Preparation of DEA Monobutoxylate
(1-[bis(2-hydroxyethyl)amino]-2-butanol)

This run targeted the butoxylation (1 BO) of Diethanolamine (DEA) without addition of catalyst (amine auto-catalytic) using a 110° C. feed temperature and a 110° C. digest temperature. DEA (1960.2 g) was charged to a 9 L reactor. The reactor was pressurized with nitrogen then vented (7 times) to remove atmospheric oxygen. Subsequently, the reactor was pressurized with nitrogen to 16-20 psia at ambient temperature. The reactor contents were heated with agitation at 110° C., then BO (1395 g total) was metered into the reactor over 2½ hr at 110° C. resulting in an operating pressure of 25-30 psia. After the BO feed was complete, the reactor contents were agitated at 110° C. for an additional 17 hr (overnight) to consume unreacted oxide (digest). The reactor was cooled to approximately 100° C., then nitrogen sparged for 1 hr to remove any unreacted butylene oxide. Subsequently, the reactor was cooled to 60° C. and drained affording 3161.4 g of product. A sample of the reaction product analyzed by hydroxyl titration (28.494% OH corresponding to 179 MW or DEA+1.0BO). Proton NMR spectroscopy provided an estimated BO:DEA molar ratio of 1.0.

Model Metalworking Fluid (MWF) Sample Preparation

Model MWF samples were prepared by weighing the components using an analytical scale. Forty grams of each model MWF concentrate sample was made.

The 40 gram blank samples (no biocide) were prepared as follows:

| | |
|---|---|
| 16.38 g | sterile Millipore water (dH$_2$0) |
| 18.8 g | Propylene Glycol |
| 2.46 g | 1M HCl |
| 2.36 g | amine |

NaOH was used to bring the final pH to 9.95-10.
The following amines were used to make up the samples:
A. 1-[bis(hydroxyl ethyl)amino]-2-butanol
B. 8-methylnonylamine diethoxylated with average 5 EO units
C. bis(2-hydroxyethyl)isodecyloxypropylamine
D. N,N-bis(2-hydroxy butyl)-2-amino ethanol
E. triethanolamine
F. 2-aminoethanol
G. TIPA
H. 3-amino-4-octanol
I. AMP 95 (2-amino-2-methylpropan-1-ol)

To prepare the dosed biocide samples, the amount of dH$_2$O was adjusted to compensate for the biocide added. NaOH was used to bring the pH to 9.95-10 prior to adding active biocide. The following recipes were used:

| MIT | |
|---|---|
| 16.28 g | dH$_2$O |
| 2.32 g | amine |
| 2.4 g | 1M HCl |
| 18.8 g | Propylene Glycol |
| 0.2 g | KORDEK LX 5000 biocide (Approx 2500 ppm MIT dosed) |

| OIT | |
|---|---|
| 16.35 g | dH2O |
| 2.32 g | amine |
| 2.4 g | 1M HCl |

| OIT | |
|---|---|
| 18.8 g | Propylene Glycol |
| 0.13 g | SKANE M8 biocide (Approx 1500 ppm OIT dosed) |

| MBIT | |
|---|---|
| 12.48 g | dH2O |
| 2.32 g | amine |
| 2.4 g | 1M HCl |
| 18.8 g | Propylene Glycol |
| 4 g | ROCIMA 551S biocide (Approx 3700 ppm MBIT dosed) |

| CMIT/MIT at tankside dilution | |
|---|---|
| 19.39 g | dH$_2$O |
| 0.058 g | amine |
| 0.06 g | 1M HCl |
| 0.47 g | Propylene Glycol |
| 0.024 g | KATHON CC biocide (Approx 18 ppm total CMIT and MIT dosed) |

Stability Testing

The MWF samples dosed with biocide were analyzed for active level by high pressure liquid chromatography (HPLC) at time 0. The samples were then vortexed and split into a sample that was aged at room temperature and a sample that was aged at 40° C. Each week an aliquot of the aged samples was evaluated by HPLC for the level of active remaining. Samples where no active was found for two consecutive weeks were no longer analyzed. The following tables display the results for each amine with each tested biocide as wt % of remaining active ingredient at the indicated time. Bold values represent acceptable levels of stability. Amines A, D and G are within the scope of claim 1; the others are comparative.

| MIT Results at Room Temperature | | | | | | | | | |
|---|---|---|---|---|---|---|---|---|---|
| week | A | B | C | D | E | F | G | H | I |
| 1 | 99 | 90 | 88 | 96 | 98 | 0 | 102 | 92 | 84 |
| 2 | 100 | 92 | 84 | 100 | 93 | 0 | 92 | 84 | 76 |
| 3 | 96 | 87 | 75 | 94 | 71 | NA | 91 | 76 | 80 |
| 4 | 99 | 88 | 67 | 97 | 0 | NA | 84 | 68 | 74 |
| 5 | 100 | 90 | 65 | 98 | 0 | NA | 89 | 68 | 77 |
| 6 | 99 | 90 | 61 | 99 | NA | NA | 89 | 67 | 77 |
| 7 | 90 | 85 | 54 | 89 | NA | NA | 88 | 61 | 75 |
| 8 | 89 | 84 | 50 | 89 | NA | NA | 133 | 58 | 77 |
| 12 | 86 | 81 | 46 | 86 | NA | NA | 93 | 50 | 78 |
| 16 | 91 | 87 | 46 | 90 | NA | NA | 94 | 36 | 80 |
| 20 | 92 | 80 | 46 | 91 | NA | NA | 95 | 35 | 80 |
| 24 | 94 | 85 | 53 | 92 | NA | NA | 89 | 14 | 73 |

| MIT Results at 40° C. | | | | | | | | | |
|---|---|---|---|---|---|---|---|---|---|
| week | A | B | C | D | E | F | G | H | I |
| 1 | 97 | 87 | 0 | 97 | 0 | 0 | 99 | 0 | 80 |
| 2 | 98 | 86 | 0 | 98 | 0 | 0 | 90 | 0 | 70 |
| 3 | 96 | 82 | NA | 95 | NA | NA | 89 | 0 | 74 |
| 4 | 96 | 86 | NA | 95 | NA | NA | 82 | NA | 67 |
| 5 | 95 | 80 | NA | 94 | NA | NA | 86 | NA | 70 |
| 6 | 95 | 90 | NA | 100 | NA | NA | 86 | NA | 69 |
| 7 | 87 | 78 | NA | 87 | NA | NA | 85 | NA | 64 |
| 8 | 86 | 76 | NA | 86 | NA | NA | 83 | NA | 65 |
| 12 | 81 | 73 | NA | 82 | NA | NA | 93 | NA | 65 |
| 16 | 83 | 72 | NA | 81 | NA | NA | 87 | NA | 62 |
| 20 | 82 | 73 | NA | 79 | NA | NA | 87 | NA | NA |
| 24 | 83 | 72 | NA | 79 | NA | NA | 78 | NA | NA |

| MIT Results: 25% Amine and 10 ppm MIT | | | |
|---|---|---|---|
| Sample ID | 1 week | 2 weeks | 3 weeks |
| Room Temp Results | | | |
| A | 117 | 114 | 107 |
| D | 103 | 82 | 70 |
| E | 0 | 0 | 0 |
| F | 0 | 0 | 0 |
| G | 118 | 109 | 97 |
| 40 C. Results | | | |
| A | 96 | 71 | 53 |
| D | 49 | 17 | 9 |
| E | 0 | 0 | 0 |
| F | 0 | 0 | 0 |
| G | 68 | 32 | 20 |

These results demonstrate that, even at extremely high ratios of amine:isothiazolone, amines A, D and G provide much better stability both at room temperature and at 40° C. than other amines

| MIT Results: 1000 ppm Amine and 2500 ppm MIT | | | |
|---|---|---|---|
| Sample ID | 1 week | 2 weeks | 3 weeks |
| Room Temp Results | | | |
| A | 105 | 108 | 106 |
| D | 105 | 108 | 106 |
| E | 105 | 107 | 106 |
| F | 106 | 108 | 106 |
| G | 107 | 110 | 107 |
| 40 C. Results | | | |
| A | 107 | 109 | 108 |
| D | 105 | 107 | 106 |
| E | 105 | 107 | 104 |
| F | 105 | 108 | 105 |
| G | 109 | 110 | 108 |

| CMIT/MIT in Tankside Dilution Fluid | | | | | | | | | | |
|---|---|---|---|---|---|---|---|---|---|---|
| week | | A | B | C | D | E | F | G | H | I |
| 1 | MIT | 100 | 126 | 100 | 100 | 100 | 100 | 100 | 137 | 100 |
|  | CMIT | 100 | 100 | 89 | 100 | 38 | 78 | 99 | 122 | 102 |
|  | MIT + CMIT | 105 | 106 | 91 | 100 | 52 | 91 | 99 | 119 | 102 |
| 2 | MIT | 115 | 132 | 129 | 126 | 121 | 147 | 131 | 128 | 122 |
|  | CMIT | 95 | 97 | 0 | 91 | 8 | 59 | 93 | 95 | 97 |
|  | MIT + CMIT | 100 | 104 | 27 | 98 | 34 | 79 | 102 | 102 | 103 |
| 3 | MIT | 100 | 108 | 98 | 99 | 95 | 102 | 98 | 91 | 101 |
|  | CMIT | 81 | 84 | 0 | 77 | 0 | 37 | 82 | 85 | 87 |
|  | MIT + CMIT | 85 | 89 | 21 | 82 | 21 | 52 | 85 | 86 | 90 |
| 4 | MIT | 89 | 99 | 0 | 92 | 89 | 90 | 91 | 91 | 95 |
|  | CMIT | 70 | 67 | 0 | 66 | 0 | 24 | 73 | 77 | 79 |
|  | MIT + CMIT | 74 | 74 | 0 | 72 | 20 | 39 | 77 | 80 | 82 |

| OIT Results in Concentrate at Room Temperature | | | | | | | | | |
|---|---|---|---|---|---|---|---|---|---|
| week | A | B | C | D | E | F | G | H | I |
| 1 | 102 | 99 | 0 | 103 | 100 | 91 | 102 | 82 | 96 |
| 2 | 100 | 90 | 0 | 101 | 72 | 82 | 101 | 0 | 90 |
| 3 | 98 | 85 | NA | 98 | 0 | 74 | 100 | 0 | 89 |
| 4 | 99 | 84 | NA | 98 | 0 | 69 | 99 | NA | 88 |
| 8 | 99 | 73 | NA | 99 | NA | 0 | 100 | NA | 87 |
| 12 | 102 | 52 | NA | 102 | NA | 0 | 101 | NA | 86 |
| 16 | 102 | 49 | NA | 102 | NA | NA | 104 | NA | 85 |
| 20 | 98 | 44 | NA | 98 | NA | NA | 100 | NA | 81 |
| 24 | 96 | 40 | NA | 96 | NA | NA | 98 | NA | 78 |

| OIT Results in Concentrate at 40° C. | | | | | | | | | |
|---|---|---|---|---|---|---|---|---|---|
| week | A | B | C | D | E | F | G | H | I |
| 1 | 100 | 64 | 0 | 100 | 0 | 0 | 101 | 1 | 90 |
| 2 | 99 | 59 | 0 | 99 | 0 | 0 | 100 | 0 | 87 |
| 3 | 98 | 55 | NA | 99 | NA | NA | 100 | 0 | 83 |
| 4 | 97 | 56 | NA | 98 | NA | NA | 101 | NA | 82 |
| 8 | 98 | 56 | NA | 98 | NA | NA | 105 | NA | 80 |
| 12 | 97 | 57 | NA | 97 | NA | NA | 108 | NA | 73 |
| 16 | 90 | 57 | NA | 97 | NA | NA | 106 | NA | 69 |
| 20 | 2 | 55 | NA | 92 | NA | NA | 103 | NA | 62 |
| 24 | 2 | 53 | NA | 62 | NA | NA | 100 | NA | 55 |

| MBIT Results in Concentrate at Room Temperature | | | | |
|---|---|---|---|---|
|  | 1 | 2 | 3 | 4 |
| A | 107 | 107 | 103 | 102 |
| B | 101 | 88 | 88 | 88 |
| C | 99 | 98 | 93 | 91 |
| D | 102 | 97 | 98 | 96 |
| E | 102 | 98 | 101 | 99 |
| F | 46 | 49 | 22 | 0 |
| G | 104 | 102 | 100 | 100 |
| H | 95 | 93 | 92 | 83 |
| I | 90 | 87 | 86 | 86 |

| MBIT Results in Concentrate at 40° C. | | | | |
|---|---|---|---|---|
|  | week 1 | week 2 | week 3 | week 4 |
| A | 104 | 96 | 98 | 97 |
| B | 89 | 87 | 85 | 85 |
| C | 83 | 85 | 84 | 79 |
| D | 98 | 95 | 94 | 94 |
| E | 43 | 47 | 47 | 44 |
| F | 21 | 54* | 22 | 28 |
| G | 101 | 98 | 96 | 95 |
| H | 90 | 12 | 17 | 40 |
| I | 85 | 79 | 76 | 72 |

The invention claimed is:

1. An aqueous composition comprising: (a) at least one 3-isothiazolone; and (b) at least one tertiary amine selected from the group consisting of N,N-bis(2-hydroxybutyl)-2-aminoethanol, 1-[bis(2-hydroxyethyl)amino]-2-butanol and triisopropanol amine.

2. The aqueous composition of claim 1 in which said at least one 3-isothiazolone is selected from the group consisting of 2-methyl-4-isothiazolin-3-one, 5-chloro-2-methyl-4-isothiazolin-3-one, N-methyl-1,2-benzisothiazolin-3-on, 2-octyl-4-isothiazolin-3-one and combinations thereof.

3. The aqueous composition of claim 2 in which the aqueous composition is a metalworking fluid or a metalworking fluid concentrate.

4. The aqueous composition of claim 3 in which the tertiary amine is present at a level from 0.1% to 25 wt % and the 3-isothiazolone is present at a level from 3 to 6000 ppm.

5. A method of producing a metalworking fluid; said method comprising combining in an aqueous composition suitable for use as a metalworking fluid: (a) at least one 3-isothiazolone; and (b) at least one tertiary amine selected from the group consisting of N,N-bis(2-hydroxybutyl)-2-aminoethanol, 1-[bis(2-hydroxyethyl)amino]-2-butanol and triisopropanol amine.

6. The method of claim 5 in which said at least one 3-isothiazolone is selected from the group consisting of 2-methyl-4-isothiazolin-3-one, 5-chloro-2-methyl-4-isothiazolin-3-one, N-methyl-1,2-benzisothiazolin-3-on, 2-octyl-4-isothiazolin-3-one and combinations thereof.

7. The method of claim 6 in which the tertiary amine is present at a level from 0.1 to 25 wt % and the 3-isothiazolone is present at a level from 3 to 6000 ppm.

8. The composition of claim 4 in which the tertiary amine is selected from the group consisting of N,N-bis(2-hydroxybutyl)-2-aminoethanol and 1-[bis(2-hydroxyethyl)amino]-2-butanol.

* * * * *